United States Patent
Su (10) Patent No.: US 9,783,467 B2
(45) Date of Patent: Oct. 10, 2017

(54) PROCESS FOR RECOVERING OLEFINS FROM MANUFACTURING OPERATIONS

(71) Applicant: Membrane Technology and Research, Inc., Newark, CA (US)

(72) Inventor: Paul Su, Saratoga, CA (US)

(73) Assignee: Membrane Technology and Research, Inc., Newark, CA (US)

( * ) Notice: Subject to any disclaimer, the term of this patent is extended or adjusted under 35 U.S.C. 154(b) by 0 days.

(21) Appl. No.: 15/341,830

(22) Filed: Nov. 2, 2016

(65) Prior Publication Data

US 2017/0050900 A1   Feb. 23, 2017

Related U.S. Application Data

(63) Continuation-in-part of application No. 14/938,546, filed on Nov. 11, 2015, now abandoned, which is a
(Continued)

(51) Int. Cl.
C07C 7/09    (2006.01)
C07C 7/00    (2006.01)
(Continued)

(52) U.S. Cl.
CPC ............ *C07C 7/005* (2013.01); *B01D 53/002* (2013.01); *B01D 53/226* (2013.01);
(Continued)

(58) Field of Classification Search
None
See application file for complete search history.

(56) References Cited

U.S. PATENT DOCUMENTS 4,623,704 A  11/1986 Dembicki et al.
5,089,033 A   2/1992 Wijmans
(Continued)

OTHER PUBLICATIONS

Kusuki, et al., "Gas Permeation Properties and Characterization of Asymmetric Carbon Membranes Prepared by Pyrolizing Asymmetric Polyimide Hollow Fiber Membrane," Journal of Membrane Science, vol. 134, pp. 245-253 (1997).
(Continued)

*Primary Examiner* — Tam M Nguyen
(74) *Attorney, Agent, or Firm* — Timothy A. Hott (57) ABSTRACT

A process for treating an effluent gas stream arising from a manufacturing operation that produces an olefin or an olefin derivative to recover unreacted olefin. The process involves compressing the effluent gas stream, which comprises an olefin, a paraffin, and a third gas, to produce a first compressed stream, then directing the first compressed stream to a membrane separation pretreatment step. The permeate stream withdrawn from this step is enriched in olefin and is sent to a second compressor, which produces a second compressed stream that is then cooled and condensed. The condensation step produces a liquid condensate and an uncondensed gas stream. The uncondensed gas stream undergoes a second membrane separation step to produce another olefin-enriched permeate stream, which is recirculated within the process prior to the second compression step, and an olefin-depleted residue stream, which may be purged from the process.

24 Claims, 6 Drawing Sheets

Related U.S. Application Data continuation-in-part of application No. 14/722,738, filed on May 27, 2015, now Pat. No. 9,216,931, and a continuation-in-part of application No. 14/789,166, filed on Jul. 1, 2015, now Pat. No. 9,309,171, which is a continuation-in-part of application No. 14/486,382, filed on Sep. 15, 2014, now Pat. No. 9,073,808, said application No. 14/722,738 is a continuation-in-part of application No. 14/486,382, filed on Sep. 15, 2014, now Pat. No. 9,073,808.

(51) Int. Cl.
  *C07C 7/144*    (2006.01)
  *F25J 3/06*     (2006.01)
  *B01D 53/00*    (2006.01)
  *B01D 53/22*    (2006.01)

(52) U.S. Cl.
  CPC .............. *B01D 53/229* (2013.01); *C07C 7/09* (2013.01); *C07C 7/144* (2013.01); *F25J 3/062* (2013.01); *B01D 53/225* (2013.01); *B01D 2256/24* (2013.01); *B01D 2257/102* (2013.01); *B01D 2257/108* (2013.01); *B01D 2257/702* (2013.01); *C01B 2203/0405* (2013.01); *F25J 2205/02* (2013.01); *F25J 2205/80* (2013.01); *F25J 2210/04* (2013.01); *F25J 2230/30* (2013.01); *F25J 2230/60* (2013.01); *F25J 2270/90* (2013.01); *Y02P 20/582* (2015.11); *Y02P 30/48* (2015.11)

(56) References Cited

U.S. PATENT DOCUMENTS

| | | |
|---|---|---|
| 5,199,962 A | 4/1993 | Wijmans |
| 5,769,927 A | 6/1998 | Gottschlich et al. |
| 5,817,841 A | 10/1998 | Baker et al. |
| 5,980,609 A | 11/1999 | Baker et al. |
| 6,118,021 A | 9/2000 | Baker et al. |
| 6,271,319 B1 | 8/2001 | Baker et al. |
| 6,414,202 B1 | 7/2002 | Baker et al. |
| 6,428,606 B1 | 8/2002 | Gottschlich et al. |
| 6,525,236 B1 | 2/2003 | Baker et al. |
| 6,899,743 B2 * | 5/2005 | Wijmans ................ B01D 3/145 210/640 |
| 7,479,227 B2 | 1/2009 | Da Costa et al. |
| 8,114,192 B2 * | 2/2012 | Baker .................... B01D 53/22 422/187 |
| 8,309,776 B2 | 11/2012 | van Egmond et al. |
| 2004/0173529 A1 | 9/2004 | Da Costa et al. |
| 2005/0154247 A1 | 7/2005 | Jong et al. |
| 2007/0232847 A1 | 10/2007 | Minhas et al. |
| 2008/0167512 A1 * | 7/2008 | Sanders ............... B01D 53/226 585/818 |
| 2011/0077446 A1 | 3/2011 | Shanbhag et al. |
| 2013/0303819 A1 | 11/2013 | Su |
| 2015/0158795 A1 * | 6/2015 | Wynn ..................... C07C 7/005 585/809 |
| 2016/0075619 A1 * | 3/2016 | Su .......................... C07C 7/144 585/809 |
| 2016/0075620 A1 * | 3/2016 | Su .......................... C07C 7/144 585/809 |

OTHER PUBLICATIONS

Lee and Hwang, "Separation of Propylene and Propane by Polyimide Hollow-Fiber Membrane Module," Journal of Membrane Science, vol. 73 pp. 37-45 (1992).

Baker, "Gas Separation," in Membrane Technology and Applications, third edition, p. 333, John Wiley and Sons, Chichester, UK (2012).

* cited by examiner

PROCESS FOR RECOVERING OLEFINS FROM MANUFACTURING OPERATIONS

CROSS-REFERENCE TO RELATED APPLICATIONS

This application is a continuation-in-part of U.S. application Ser. No. 14/938,546, filed on Nov. 11, 2015, now abandoned, which is a continuation-in-part of U.S. application Ser. No. 14/722,738, filed on May 27, 2015, which is as U.S. Pat. No. 9,216,931 on Dec. 22, 2015, and is also a continuation-in-part of U.S. application Ser. No. 14/789,166, filed on Jul. 1, 2015, which issued as U.S. Pat. No. 9,309,171 on Apr. 12, 2016, which are both continuation-in-parts of U.S. application Ser. No. 14/486,382, filed Sep. 15, 2014, which issued as U.S. Pat. No. 9,073,808 on Jul. 7, 2015, the disclosures of all of which are hereby incorporated herein by reference in their entireties.

FIELD OF THE INVENTION

The invention relates to a process for recovering olefins from a manufacturing operation. More specifically, the invention relates to treating an effluent gas stream using membranes for recovering olefin and separating paraffin.

BACKGROUND OF THE INVENTION

Olefins, such as ethylene and propylene, and their non-polymeric derivatives, such as isopropyl alcohol and cumene, account for some of the most demanded chemicals in the world. For example, the United States alone produces more than 10 billion pounds of chemicals derived from propylene annually.

Olefins are commonly produced by cracking hydrocarbon feedstocks or catalytically converting oxygenate feedstocks. Traditional methods for cracking include steam cracking, whereby naphtha or other hydrocarbons are reacted with steam to make light olefins, and fluid catalytic cracking (FCC), which is the refinery operation that breaks down larger hydrocarbons to produce naphtha-light components for gasoline, as well us olefins and heating oils. The conventional conversion of oxygenate feedstocks includes methanol-to-olefin (MTO) and methanol-to-propylene (MTP) processes. In MTO, methanol is converted primarily to ethylene and propylene in the presence of a molecular sieve catalyst. In MTP, methanol is dehydrated to produce dimethyl ether, which is then converted to propylene. Both processes involve complex operations downstream of the reactor(s) to purify the product, capture unconverted reagents for recycle, and purge contaminants. Typically, low temperature partial condensation is involved, and at least a portion of the uncondensed gas is recycled in the process.

In non-polymeric olefin derivative manufacturing, an olefin and other reagents are introduced into a high-pressure reactor. The raw effluent from the reactor is transferred continuously to one or more separation steps, from which a stream of raw derivative product is withdrawn for further purification. A stream of overhead gases, containing unreacted olefin, is also withdrawn from the separation steps and is recirculated back to the reactor.

Both of these types of manufacturing operations need to vent a portion of uncondensed gas to prevent build-up of unwanted contaminants in the reaction loop. However, the vented overhead gas typically contains unreacted olefin that, without further treatment, would otherwise go to waste.

Additionally, polyethylene (PE) and polypropylene (PP) are two of the most demanded polymers in the world. Together, these polymers make up half of the volume of plastic produced worldwide.

During polyolefin production, a small portion of the olefin feedstock is lost through raw material purification, chemical reaction, and product purification and finishing. In particular, paraffin that enters with the olefin feedstock must be removed to prevent its build up in the reactor loop, and olefin is lost when this paraffin is purged from the loop. This results in an annual loss of $1 million to $3 million per year for a typical polyolefin plant. The development of a more efficient way to prevent the loss of olefin monomer in the feedstock has been an on-going process for those in the petrochemical field.

In polyolefin manufacturing, a feedstock containing olefin monomer, catalysts, and other agents is introduced into a high-pressure polymerization reactor. During the reaction, a raw polymer product is produced. The raw product contains polyolefin, significant amounts of unreached olefin, and small amounts of solvents, catalysts, stabilizers, other hydrocarbons or any other materials, depending on the manufacturing process used. To remove the volatile contaminants dissolved in the raw product, it is passed to large bins, where nitrogen is used to purge them out. The vent gas from this step contains nitrogen, unreacted olefin monomer, unwanted analogue paraffins that entered with the olefin feedstock, and other process-specific materials. In the past, this vent gas was sent for flaring, resulting in a waste of unreacted olefin.

Various process and techniques have been proposed for mitigating the loss of unreacted olefin in a variety of streams.

U.S. Pat. No. 4,623,704, to Dembicki et al. (Dow Chemical Company), discloses a process for treating a polymerization vent gas with a membrane. The vent stream is compressed and then cooled and condensed. Cooled gas and liquid are sent to a liquid/gas separator. After separation, the gas stream is sent through a series of membrane separation steps, which produce a permeate stream enriched in ethylene. The recovered ethylene is recycled to the polymerization process.

Co-owned U.S. Pat. Nos. 5,089,033 and 5,199,962, to Wijmans (Membrane Technology and Research, Inc.), disclose processes for recovering a condensable component in a gas stream that would otherwise be discharged into the atmosphere. The processes involve a condensation step and a membrane separation step. In one embodiment, the gas stream is compressed and cooled to carry out the condensation step. Uncondensed gas is then passed across a membrane that is selectively permeable to the condensable component.

Co-owned U.S. Pat. No. 6,271,319, to Baker et al. (Membrane Technology and Research, Inc.), discloses a process for treating the uncondensed gas stream using a gas separation membrane that is permeable for propylene over propane. A permeate stream enriched in olefin is withdrawn and recycled to the reactor inlet.

These patents, and other prior art technologies, have mainly focused on condensing a gas stream and recovering unreacted olefin from the resulting uncondensed gas produced from the condensation step. However, little is taught on recovering olefins from the effluent stream in a membrane separation pretreatment step prior to undergoing the main compression, condensation, and membrane separation steps as in prior art processes.

Co-owned U.S. Pat. No. 5,769,927, to Gottschlich et al. (Membrane Technology and Research, Inc.), discloses a process for treating a purge vent stream from a polymer manufacturing operation. The purge vent stream contains an unreacted olefin monomer and nitrogen. The purge vent stream is initially treated in a condensation step. The uncondensed gas is then passed to a membrane separation step, where the membrane is organic-selective, meaning that the membrane is selective for unreacted monomer over other gases. The liquid condensate is directed to a flash evaporation step. The flashing step produces a liquid product stream enriched in monomer and a flash gas that is recirculated in the process.

Despite the above improvements, there remains a need for better olefin recovery technology applicable to processes that make or use olefins or olefin derivatives.

SUMMARY OF THE INVENTION

Accordingly, the present invention relates to a process for recovering olefins by treating an effluent gas stream comprising an olefin, a paraffin, and a third gas. The effluent stream is withdrawn from either an olefin or an olefin derivative (including polyolefin and non-polymeric) manufacturing operation. During treatment, the effluent gas stream is compressed in a first compressor and then directed to a first membrane separation pretreatment step to produce a first olefin-enriched permeate stream and a first olefin-depleted residue stream. The first residue stream, depleted in olefin, is purged from the process. The first permeate stream, enriched in olefin, is passed to a second compressor and then condensed and separated, producing a liquid condensate stream and an uncondensed gas stream. The uncondensed gas stream undergoes treatment by a second membrane separation step to produce a second olefin-enriched permeate stream and a second olefin-depleted residue stream. The second olefin-enriched permeate stream is recycled upstream of the second compressor while the second olefin-depleted stream is purged. Unreacted olefin is recovered in the liquid condensate stream, which may be sent in a recycle loop for use as feedstock back in the manufacturing operation.

Therefore, in a basic embodiment, the process of the invention includes the following steps:

(a) compressing said effluent gas stream using a first compressor to produce a first compressed gas stream;

(b) separating the first compressed stream gas stream using a first membrane to produce a first olefin-enriched permeate stream and a first olefin-depleted residue stream;

(c) compressing the first olefin-enriched permeate stream using a second compressor to produce a second compressed gas stream;

(d) partially condensing the second compressed stream, including cooling and separating the compressed stream into an uncondensed gas stream depleted in olefin and paraffin and a condensed liquid condensate enriched in olefin and paraffin;

(e) separating the uncondensed gas stream using a second membrane to produce a second olefin-enriched permeate stream and a second olefin-depleted residue stream; and (f) returning the second olefin-enriched permeate stream upstream of the second compressor.

In certain embodiments, the effluent gas stream of step (a) may arise from the following three types of manufacturing operations:

The first type is an operation that produces olefins. These operations include, but are not limited to, fluid catalytic cracking, olefin cracking, steam cracking, olefin metathesis, a methanol-to-olefin process (MTO), and a methanol-to-propylene (MTP) process.

The second type is an operation that manufactures a non-polymeric olefin derivative, using olefins as a feedstock. Non-limiting examples of these operations include chlorohydrin production, butyraldehyde production, oxo alcohol production, isopropyl alcohol production, acrylic acid production, allyl chloride production, allyl alcohol production, acrylonitrile production, cumene production, ethylene oxide production, vinyl acetate production, ethylene dichloride production, ethanol production, and ethyl benzene production.

The third type is an operation that produces a polyolefin. In a polyolefin manufacturing plant, the effluent stream is vented from a purge bin. The effluent stream from this type of process is typically referred to as a "purge stream," but is used interchangeably herein with "effluent stream."

In all cases, the effluent gas stream comprises an olefin, an analogous paraffin, and a third gas. In certain aspects, the olefin is ethylene or propylene. In other aspects, the olefin is butylene. The effluent gas stream may also comprise multiple sets of olefins and analogous paraffins, for example, ethane/ethylene and propane/propylene. The effluent gas stream also contains a third gas, such as methane, hydrogen, or nitrogen.

A driving force for transmembrane permeation is provided by a pressure difference between the feed and permeate side of the membrane. In step (a), this is achieved by compressing the effluent stream, which is typically at a low pressure, to an elevated pressure on the feed side of the membrane. In other aspects, the driving force can be produced by drawing a vacuum on the permeate side of the membrane, or a combination of both compression and vacuum can also be used.

In step (b), the first membrane separation step may be carried out in a membrane unit containing a membrane or membranes that are selectively permeable to olefins over paraffins and inorganic gases to produce a first permeate stream enriched in olefin and a first residue stream depleted in olefin. Two options are possible here. The first can be used if it is more important to separate the olefin and paraffin together into the permeate stream, leaving a residue stream that is depleted in all $C_{2+}$ hydrocarbons. For this option, a membrane should be chosen that has good selectivity between the $C_{2+}$ hydrocarbons as a group and the inorganic gases. This may be the situation, for example, if the permeate stream can be passed back to a unit operation where the olefins and paraffins can be separated effectively, or if the inorganic gas is to be purged or recycled and should have a low overall hydrocarbon content.

Any membrane with suitable performance properties may be used. Typically, for this option, these membranes are polymeric and preferably have a selective layer that comprises a rubbery or elastomeric polymer. Representative preferred membranes include, but are not limited to, nitrile rubber, neoprene, polydimethylsiloxane (silicone rubber), chlorosulfonated polyethylene, polysilicone-carbonate copolymers, and fluoroelastomers. Silicone rubber is the most preferred material for use in this step.

The second option is useful if it is more important to achieve a permeate stream with a high concentration of olefins and relatively little paraffin. A membrane that offers good selectivity between olefins and paraffins in addition to good selectivity between olefins and inorganic gases is needed.

These membranes are preferably inorganic membranes. Inorganic membranes with olefin/paraffin separating properties are very finely porous and act as very fine sieves that separate on the basis of polarity difference. Inorganic membranes are characterized by good temperature and chemical resistance. More preferably, the inorganic membranes are zeolite membranes. Such membranes include, but are not limited to, zeolite-based membranes that are crystalline oxides consisting of silicon, aluminum, and other cations, such as sodium and potassium coated on ceramic or other types of support structures.

Advantageously, inorganic membranes exhibit good separation properties for feed streams at low pressure with high inert gas content. Thus, these membranes are a good option for the membrane separation pretreatment step.

In certain aspects, membranes for separating olefins and paraffins may include polymeric membranes. Typically, these membranes have a selective layer made from a glassy polymer. Representative examples of these membranes include, but are not limited to, poly(phenylene oxide) (PPO), polyimides, perflourinated polyimides, Hyflon® AD, and Cytop®.

In other aspects, the membranes used in the first membrane separation step may include facilitated transport membranes. These contain a liquid that itself contains, for example, free silver ions that react selectively and reversibly with unsaturated hydrocarbons, to selectively carry olefin, such as propylene, across the membrane.

The goal of steps (c) and (d) is to bring the first olefin-enriched permeate stream to a pressure/temperature condition beyond, the dewpoint of the olefin to be recovered, so that a portion of the olefin will condense out of the gas stream. Thus, the separation of the compressed stream creates a liquid condensate and an uncondensed (residual) gas stream. The condensate is enriched in olefin and the uncondensed gas stream is depleted in olefin relative to the first olefin-enriched permeate stream.

The condensation step usually involves chilling and compression. Compressing the gas raises the dewpoint temperature, so a combination of compression and chilling is generally preferred.

In step (e), the uncondensed gas stream from step (d) is passed as a feed stream and treated in a second membrane separation step. The membranes in step (d) are selectively permeable to olefins over paraffins and inorganic gases using a similar type of membrane as described above for the first membrane separation step. A second permeate stream enriched in olefins and a second residue stream depleted in olefins are withdrawn from the membrane.

In step (f), the second permeate stream from step (e) is recycled upstream of the compressor of step (c) for further olefin recovery.

In certain embodiments, especially in cases where a polymeric membrane that is selective for $C_{2+}$ hydrocarbons over other gases is used in the first membrane separation step, it may be desirable to further treat the liquid condensate from step (d) in a third membrane separation step to recover olefin. The membrane used in this step is selective for olefin over paraffin and is preferably inorganic. This step thus results in a third permeate stream enriched in olefin and a third residue stream depleted in olefin.

This third separation step may be carried out under pervaporation or vapor permeation conditions.

In other embodiments, the second olefin-depleted residue stream is further separated using a third membrane separation step. The membrane used in this step is selectively permeable to olefins, and optionally paraffin, over other gases and is preferably polymeric. This step thus results in a third permeate stream enriched in olefin and a third residue stream depleted in olefin. The permeate stream may be sent off to flare or any other suitable destination while the residue stream, typically containing a high percentage of the third gas, may be sent to any desired destination within or outside of the manufacturing operation, or simply vented or purged.

In a further embodiment, the first olefin-depleted residue stream is further separated using an additional membrane separation step to produce an olefin-enriched permeate stream and a olefin-depleted residue stream. The membrane used in this step is selectively permeable to olefins over paraffins and inorganic gases and may be either polymeric or inorganic. To recover more of the separated olefin, the olefin-enriched permeate stream may be returned upstream of the first compressor.

In yet another embodiment, the olefin-depleted residue stream from the previous embodiment is further separated using another membrane separation step. In some cases, the membrane used in this step is selective to olefin over paraffin and inorganic gases and may be either polymeric or inorganic. In other cases, the membrane may be selective to the third gas, such as nitrogen, over $C_{2+}$ hydrocarbons. The third gas may be sent to any desired destination, such as back to a polyolefin manufacturing operation in the case where nitrogen is the third gas.

Occasionally, the conditions of the process may be such that the effluent gas stream is already at high pressure. In this case, the first compression step may be dispensed with and the effluent gas stream may be sent directly to the first membrane separation step. Thus, in an alternative embodiment, the process comprises the steps of:

(a) separating the effluent stream gas stream using a first membrane to produce a first olefin-enriched permeate stream and a first olefin-depleted residue stream;

(b) compressing the first olefin-enriched permeate stream using a first, compressor to produce a first compressed gas stream;

(c) partially condensing the compressed stream, including cooling and separating the compressed stream into an uncondensed gas stream depleted in olefin and paraffin and a condensed liquid condensate enriched in olefin and paraffin; and (d) separating the uncondensed gas stream using a second membrane to produce a second olefin-enriched permeate stream and a second olefin-depleted residue stream; and (e) returning the second olefin-enriched permeate stream upstream of the first compressor.

In a further embodiment, the above process comprises the steps of:

(f) separating the first olefin-depleted residue stream using a third membrane to produce a third olefin-enriched permeate stream and a third olefin-depleted residue stream;

(g) compressing the third olefin-enriched permeate stream using a second compressor to produce a second compressed gas stream; and (h) returning the second compressed gas stream upstream of step (a).

It is to be understood that the above summary and the following detailed description are intended to explain and illustrate the invention without restricting it in scope.

DETAILED DESCRIPTION OF THE INVENTION

The term "effluent gas stream" as used herein is construed as including a gas stream withdrawn from any unit operation or operations during an olefin, polyolefin, or a non-polymeric olefin derivative manufacturing operation. As referred to herein, "effluent gas stream" also includes the term "purge stream," which is typically the name given to a stream withdrawn from a polymer manufacturing operation.

The term "olefin" as used herein means a member of the family of unsaturated, hydrocarbons having a carbon-carbon double bond of the series $C_nH_{2n}$, including members in which at least one halogen atom has been substituted for one of the hydrogen atoms.

The term "non-polymeric olefin derivative" as used herein refers to a product made from at least one olefin, wherein the product does not contain repeating units of the olefin derivative monomer. Examples of propylene derivatives include, but are not limited to, chlorohydrin (a precursor of propylene oxide); butyraldehyde (a precursor to butyl alcohol); oxo alcohols, such as 2-methyl-2-butanol, n-butanol, 2-ethylhexanol, isononyl alcohol, and isodecyl alcohol; isopropyl alcohol; acrylic acid; allyl chloride; acrylonitrile; and cumene. Examples of ethylene derivatives include, but are not limited to, ethylene oxide, vinyl acetate, ethylene dichloride, ethanol, and ethylbenzene.

The term "$C_{2+}$ hydrocarbon" means a hydrocarbon having at least two carbon atoms.

The invention relates to an improved process for recovering unreacted olefin from an effluent gas stream, comprising an olefin, a paraffin, and a third gas that arises from an olefin or olefin derivative manufacturing operation. The process also provides for selectively purging paraffin from the reactor loop. By a reactor loop, we mean a configuration in which at least a part of the effluent or purge gas stream from the reactor is recirculated directly or indirectly to the reactor. The process can be applied to any loop in which olefin is fed to the reactor, and in which olefin and paraffin are present in the effluent or purge gas steam from the reaction loop.

Figure 1:
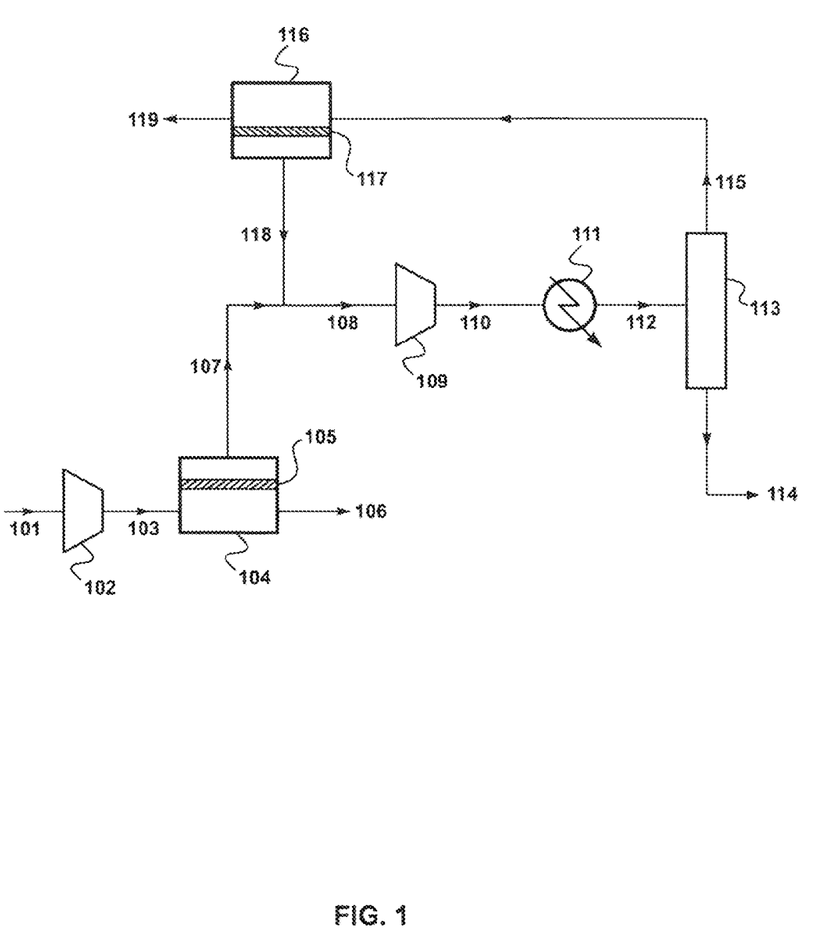
FIG. 1 is a schematic drawing showing an olefin recovery process comprising two membrane separation steps according to a basic embodiment of the invention.

It will be appreciated by those of skill in the art that FIG. 1 and the other figures showing process schemes herein are very simple block diagrams, intended to make clear the key unit operations of the embodiment processes of the invention, and that actual process trains may include many additional steps of standard type, such as heating, chilling, compressing, condensing, pumping, various types of separation and/or fractionation, as well as monitoring of pressures, temperatures, flows, and the like. It will also be appreciated by those of skill in the art that the details of the unit operations may differ from process to process.

A basic embodiment of the olefin recovery process is shown in FIG. 1.

A feed gas stream, 101, from a manufacturing process typically contains at least an unreacted olefin, an analogous paraffin, and a third gas. For purposes of FIG. 1 and the following Examples, the feed gas stream is assumed to be an effluent gas stream that is withdrawn from either a manufacturing operation that produces olefins or a manufacturing operation that uses olefins as a feedstock to produce non-polymeric olefin-derivatives. However, as discussed above, the feed gas stream may also be a purge gas stream arising from a polymer manufacturing operation.

Such non-limiting examples of processes that produce olefins include fluid catalytic cracking, olefin cracking, steam cracking, olefin metathesis, a methanol-to-olefin process (MTO), and a methanol-to-propylene (MTP) process. A reference that provides discussion of design and operation of modern FCC units, a typical source of low-molecular weight olefins, is described in Chapter 3 of "Handbook of Petroleum Refining Processes" Second Edition, R. A. Meyers (Ed), McGraw Hill, 1997, incorporated by reference herein. The other processes are well known in the art and do not require any lengthy description herein.

For olefin-derivative manufacturing processes, non-limiting examples include the production of chlorohydrin (a precursor of propylene oxide), butyraldehyde (a precursor of butyl alcohol), isopropyl alcohol, acrylic acid, allyl chloride, acrylonitrile, cumene, ethylene oxide, vinyl acetate, ethylene dichloride, ethanol, and ethylbenzene.

The third gas in the effluent (or purge) gas stream is typically, but not always, methane or an inorganic gas, such as hydrogen, nitrogen or argon. The third gas also has a lower boiling point than both the principal olefin and the principal paraffin in the effluent gas stream. Gases of this type are inevitably present in streams coming from the operations in the manufacturing train, often because they are carried in as unwanted contaminants with the feedstock, and sometimes because they are used in the reactors or the product purification steps and have intrinsic value in the manufacturing process if they could be separated and recovered.

The ratio of olefin to paraffin in the stream may be as much as 5:1, 6:1 or even 7:1 or more. If this stream were to be vented from the manufacturing process without further treatment, then as many as five, six, or seven volumes of olefin would be lost for every volume of paraffin that is purged.

Returning to FIG. 1, an effluent gas stream, 101, is routed to first compression step 102, the goal of which is to provide a driving force for first membrane separation step, 104. The first compression step may be carried out using compression equipment of any convenient type, and may be performed in one stage or in a multistage compression train, depending on the degree of compression needed. It is preferred that the pressure to which stream 101 is raised be no more than about 15 bara, and more preferably no more than about 10 bara.

The stream emerging from first compression step 102 is first compressed stream 103. In some cases, depending on the process conditions, stream 103 may be cooled prior to undergoing separation in the membrane pretreatment step. Cooling may be performed in any manner, and in one or more sub-steps, including, but not limited to, simple air or water aftercooling of the compressor outlet gases, heat exchange against other on-site process streams, chilling by external refrigerants, and any combinations of these.

Stream 103 is then sent to first membrane separation step 104. For this step, any membrane with suitable performance properties may be used. The membrane or membranes, 105, to be used in step 104 are made of any material suitable for selectively permeating olefin over paraffin and inorganic gases.

In cases where membrane separation step 104 is carried out to separate the olefin and paraffin together into the permeate stream, the membranes preferably have a selectivity for $C_{2+}$ hydrocarbons over other gases of at least about 5, more preferably greater than 10, and a hydrocarbon permeance of at least about 400 gpu. The membrane does not need much, if any, selectivity between olefins and paraffins.

Typically, for this option, these membranes are polymeric and preferably have a selective layer that comprises a rubbery or elastomeric polymer. Representative preferred membranes include, but are not limited to, nitrite rubber, neoprene, polydimethylsiloxane (silicone rubber), chlorosulfonated polyethylene, polysilicone-carbonate copolymers, and fluoroelastomers. Silicone rubber is the most preferred material for use in this step.

In cases where membrane separation step 104 is carried out to separate olefins from paraffins, membrane(s) 105 must offer good selectivity between olefins and paraffins. Preferably, the membranes provide propylene/propane selectivity of at least 5 and propylene flux of 400 gpu under favorable conditions. For ethylene/ethane separation, the preferred selectivity of the membrane is 3 and the preferred ethylene flux is 400 gpu. For butylene/butane separation, the preferred selectivity of the membrane is at least 5 and the preferred ethylene flux is 400 gpu.

These membranes are preferably inorganic membranes. Inorganic membranes with olefin/paraffin separating properties are very finely porous and act as very fine sieves that separate on the basis of polarity difference. Inorganic membranes are characterized by good temperature and chemical resistance. More preferably, the inorganic membranes are zeolite membranes. Such membranes include, but are not limited to, zeolite-based membranes that are crystalline oxides consisting of silicon, aluminum, and other cations, such as sodium and potassium coated on ceramic or other types of support structures.

In some embodiments, membranes for separating olefin and paraffin may include polymeric membranes. Typically, these membranes have a selective layer made from a glassy polymer. Representative examples of these membranes include, but are not limited to, poly(phenylene oxide) (PPO), polyimides, perflourinated polyimides, Hyflon® AD, and Cytop®.

In other embodiments, the membranes used in step 104 may include facilitated transport membranes. These contain a liquid that itself contains, for example, free silver ions that react selectively and reversibly with unsaturated hydrocarbons, to selectively carry olefin (propylene) across the membrane.

The membranes may take the form of a homogeneous film, an integral asymmetric membrane, a multilayer composite membrane, a membrane incorporating a gel or a liquid layer or particulates, or any other form known in the art.

The membranes may be manufactured as flat sheets or as hollow fibers and housed in any convenient module form, including spiral-wound modules, tubular modules, plate-and-frame modules, and potted hollow-fiber modules. The making of all these types of membranes and modules is well-known in the art.

The membrane separation steps disclosed herein may be carried out using a single membrane module or a bank of membrane modules or an array of modules. A single unit or stage containing on or a bank of membrane modules is adequate for many applications. If either the residue or permeate stream, or both, requires fusilier olefin removal, it may be passed to a second bank of membrane modules for a second processing step. Such multi-stage or multi-step processes, and variants thereof, will be familiar to those of skill in the art, who will appreciate that the membrane separation step may be configured in many possible ways, including single-stage, multistage, multistep, or more complicated arrays of two or more units, in serial or cascade arrangements.

A residue stream, 106, that is depleted in olefin relative to stream 103, is withdrawn from the feed side of the membrane. The membrane separation step reduces the olefin content of this stream, preferably to the point that the ratio of olefin to paraffin in the stream is reduced to about 4:1, or about 1:1, and more preferably below 1:1. Additionally, in some aspects, stream 106 may contain a substantial amount of third gas, preferably containing the third gas, such as nitrogen, in purified form, where the content of the third gas is at least 99%. In any case, this stream may be recycled back to the manufacturing operation, purged from the process with comparatively little loss of olefin, or may be further treated to recover any remaining unreacted olefin.

The permeate stream, 107, is enriched in olefin relative to the first compressed stream, 103. This stream is mixed with a permeate stream, 118, that is also enriched in olefin from a second membrane separation step, 116, to produce combined stream 108. Stream 108 is then sent to a second compression step, 109. It is preferred that the pressure to which stream 108 is raised be no more than about 30 bara, and more preferably no more than about 25 bara.

The stream emerging from second compression step 109 is second compressed stream 110. This stream is sent to a condensation step, 111. The condensation step includes cooling of stream 110 to below the olefin dewpoint temperature, such that a major portion of the olefin is condensed, followed by separation of the resulting liquid and gas phases. Cooling may be performed in any manner, and in one or more sub-steps, including, but not limited to, simple air or water aftercooling of the compressor outlet gases, heat exchange against other on-site process streams, chilling by external refrigerants, and any combinations of these. Preferably, this step should cool stream 110 to a temperature no lower than 30° C., and yet more preferably to no colder than about 40° C.

The liquid and gas phases that are formed by compression and cooling are separated by conventional means in a simple phase separator, knock-out drum or the like, 113, to yield condensed liquid stream, 114, and uncondensed gas stream, 115. The condensed liquid stream 114 typically comprises 80 mol %, 90 mol %, or more olefin and paraffin.

Uncondensed gas stream, 115, is depleted in olefin and paraffin and is sent for treatment to a second membrane separation step, 116. Prior to this, it may be desirable to heat stream 115 to recover heat and/or to have optimal operating temperatures. Heating of stream 115 may be accomplished by in any way, for example by heat exchange against other on-site process stream or with steam. In FIG. 1, the heat exchange may occur between hot compressed gas stream 110 and cold uncondensed gas stream 115.

The membrane or membranes, 117, to be used in step 116 are made of any material suitable for selectively permeating olefins over paraffins and inorganic gases. Preferred membrane materials are similar to the types of membranes that can be used in the first membrane separation step, 104, as described above.

Stream 115 flows across the feed side of membrane 117. A residue stream, 119, that is depleted in olefin, and optionally paraffin, relative to stream 115, is withdrawn from the feed side of the membrane. This stream typically contains a high percentage of the third gas, such as nitrogen, hydrogen, or methane and may be sent to any desired destination within or outside of the manufacturing operation, or simply vented or purged. The permeate stream, 118, is enriched in olefin, and optionally paraffin, compared with the membrane feed. Stream 118 is then recycled and combined with the first olefin-enriched permeate stream, 107, upstream of second compression step 109.

Figure 2:
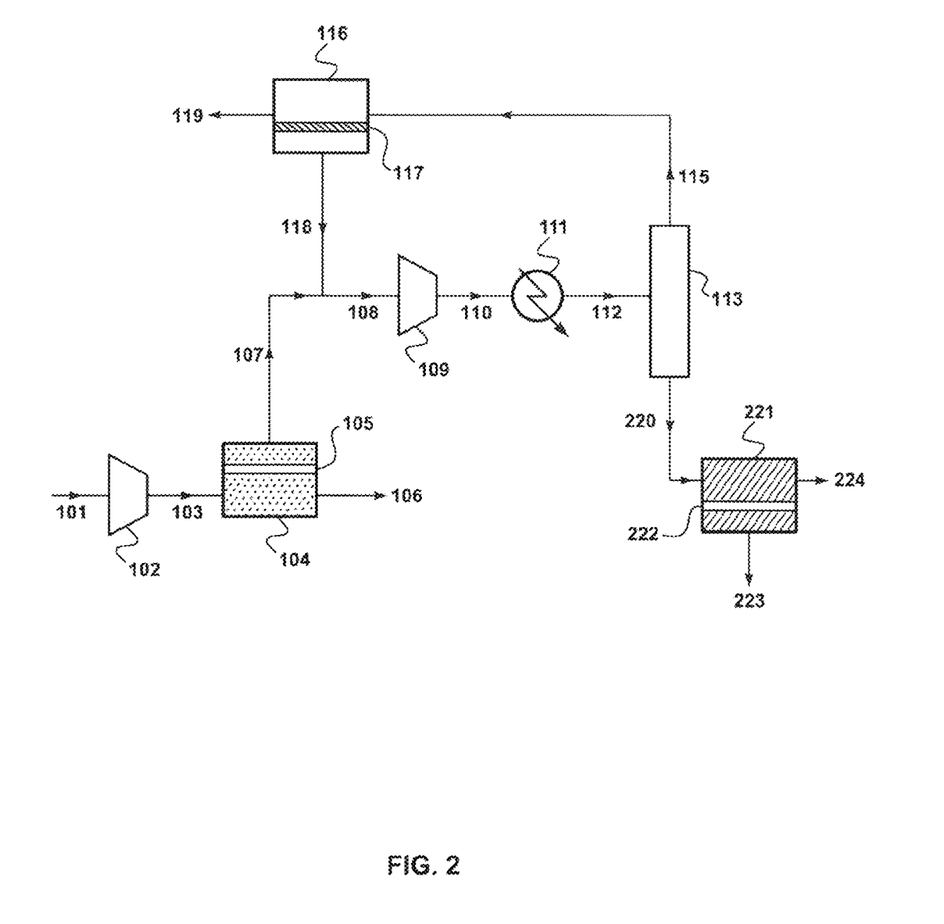
FIG. 2 is a schematic drawing showing a process scheme for a variant of the process of FIG. 1, comprising a third membrane separation step for treating the condensate stream.

Another embodiment of the olefin, recovery process is shown in FIG. 2. This embodiment is similar to that of FIG. 1 in that the first compressed stream, 103, and the uncondensed stream, 115, undergo membrane separation. However, the condensed liquid stream, 220, is further treated by a third membrane separation step, 221. This particular embodiment is typically preferred when the membrane or membranes 105 for the first membrane separation step 104 are polymeric membranes that separate $C_{2+}$ hydrocarbons and inorganic gases.

Stream 220 acts as a feed stream and passes across membrane 222 that is selectively permeable to olefins over paraffins. The residue stream, 224, contains a major part/most of the paraffin in the feed gas stream 101 and is purged from the process. The permeate stream, 223, is enriched, in olefin and may be sent to any desired application or may recycled to a number of locations within the process.

In FIG. 2, the third membrane separation step, 221, occurs under pervaporation conditions. By "pervaporation conditions" we mean that the feed is heated to elevate its vapor pressure but maintained at a sufficiently high pressure to prevent evaporation on the feed side of the membrane. The permeate side is maintained at a pressure substantially below the vapor pressure of the feed so vapor will permeate the membrane. If membrane separation step 221 occurs under pervaporation conditions, liquid stream 220 is first heated (not shown) and then flows to and across the feed side of membrane 222. The low pressure permeate vapor, enriched in the more permeable component, may optionally be cooled and condensed or may be compressed and condensed or a combination of the two.

In other embodiments, membrane separation step 221 may occur under vapor permeation conditions. In this case, liquid stream 220 is heated by a heater (not shown) of any convenient type to produce a heated vaporized stream before flowing across the feed side of membrane 222.

Under either condition, the membrane separation step reduces the olefin content of residue stream 224, preferably to the point that the ratio of olefin to paraffin in the stream is reduced to about 4:1, or to about 1:1, and more preferably below 1:1. This stream may be purged from the process with comparatively little loss of olefin.

The permeate stream, 223, is enriched in olefin compared with the membrane feed. Optionally, in certain embodiments, this stream may be used as a coolant for heat recovery at various locations within the process to minimize refrigerant energy usage. For example, permeate stream 223 may be used as a coolant in the heat-exchange/condensation step 111, emerging as warmed permeate stream.

Alternatively, if membrane separation step 221 takes place under pervaporation conditions, it may be more beneficial to cool and condense stream 223 to provide or augment the driving force for the pervaporation step.

Permeate stream 223 represents a substantial source of recovered olefin, preferably containing a chemical grade olefin, having an olefin content of at least 90%. In a preferred embodiment, permeate stream 223 is returned as feedstock to the manufacturing reactor.

In some embodiments, residue stream 224 may be treated by an additional membrane separation step using a membrane selective for olefin over paraffin in order to recover more unreacted olefin, thereby further reducing the olefin to paraffin ratio.

Preferred membranes materials for third membrane separation step 221 are similar to the inorganic membranes described above.

Figure 3:
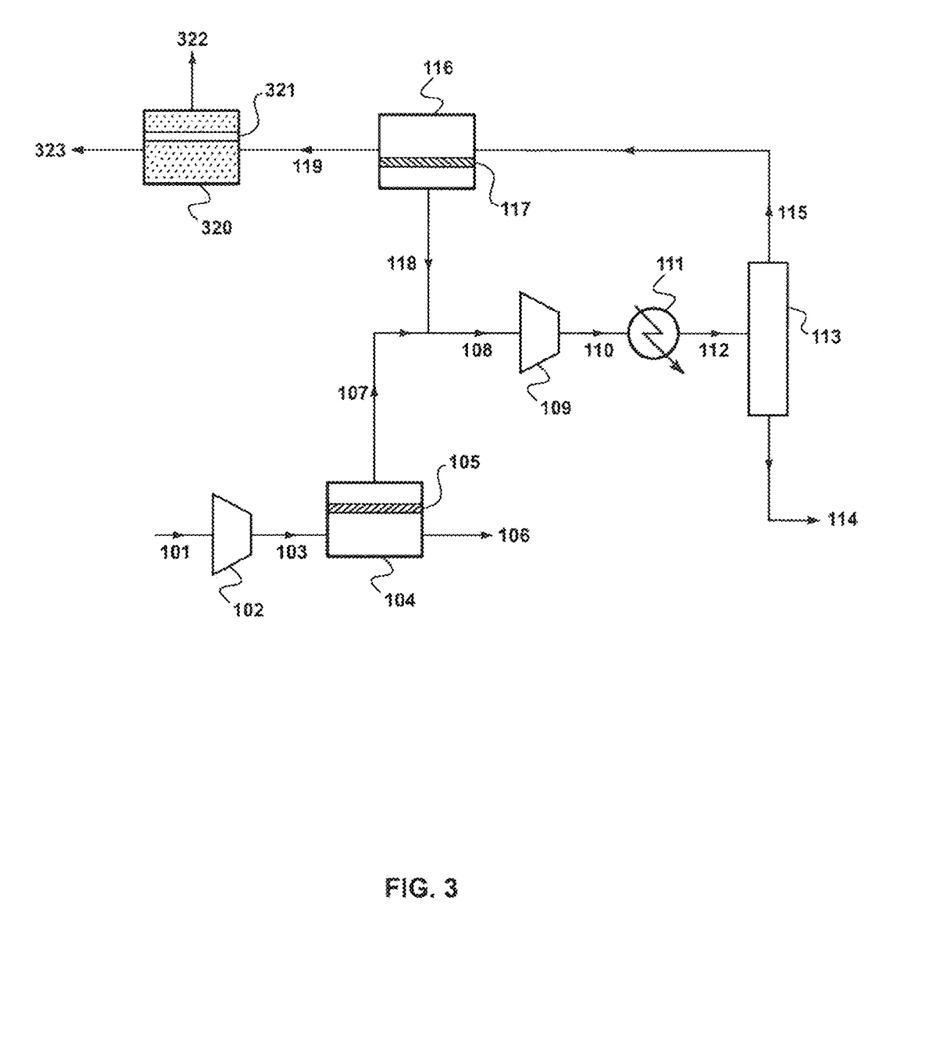
FIG. 3 is a schematic drawing showing a process scheme for a variant of the process of FIG. 1, comprising a third membrane separation step for treating the second olefin-depleted residue stream of the second membrane separation step.

Another embodiment of the olefin recovery process is shown in FIG. 3. This embodiment is similar to that of FIG. 1 in that the first compressed stream, 103, and uncondensed gas stream 115 undergo membrane separation. However, residue stream 119 is further treated by a third membrane separation step, 320.

Stream 119 acts as a feed stream and passes across membrane 321 that is selectively permeable to $C_{2+}$ hydrocarbons over other gases. The residue stream, 323, contains a high percentage of waste gases, such as nitrogen and methane, and essentially no olefin, and may be sent to any desired destination within or outside of the manufacturing operation, or simply vented or purged.

The permeate stream, 322, may be sent off to flare or any other suitable destination. The ratio of olefin to paraffin in stream 322 is preferably reduced to about 4:1, or about 1:1, and more preferably below 1:1 so that this stream may be purged from the process with comparatively little loss of olefin.

For membrane separation step 320, the preferred membrane materials are similar to the polymeric membranes described above.

Figure 4:
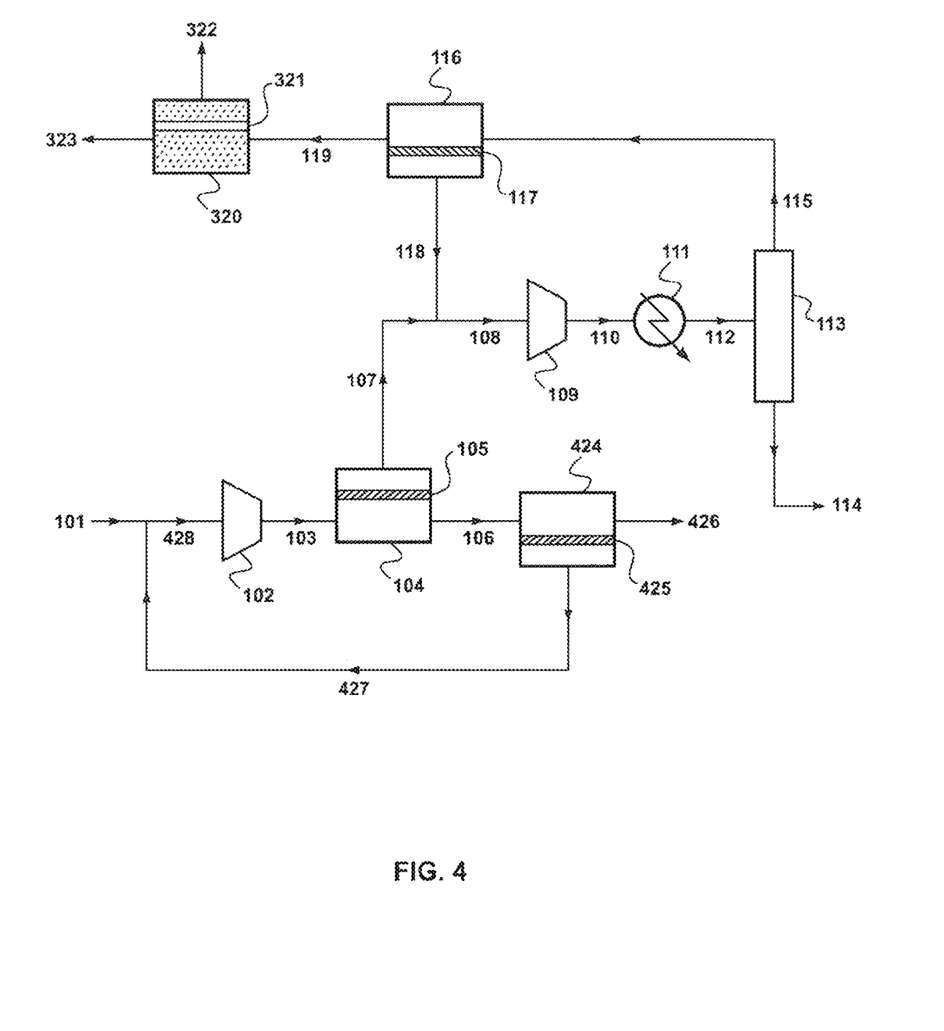
FIG. 4 is a schematic drawing showing a process scheme for a variant of the process of FIG. 3, comprising a fourth membrane separation step for treating the first olefin-depleted residue stream of the first membrane separation step.

Another embodiment of the olefin recovery process is shown in FIG. 4. This embodiment is similar to that of FIG. 3 in that the first compressed stream, 103, the uncondensed gas stream 115, and residue stream 119 all undergo membrane separation. In this case, however, residue stream 106, which is depleted in olefin relative to stream 103, is further treated by a fourth membrane separation step, 424.

Stream 106 is passed as a feed stream across the feed side of membrane 425 that is selectively permeable to olefins, and optionally paraffins, over other gases. The residue stream, 426, typically contains a high percentage of the third gas, such as nitrogen, hydrogen, or methane and may be sent to any desired destination within or outside of the manufacturing operation, or simply vented or purged. The permeate stream, 427, is enriched in olefin and is recycled upstream of first compression step 102.

The membrane or membranes used for membrane separation step 424 may be similar to the polymeric or inorganic membranes described above.

Figure 5:
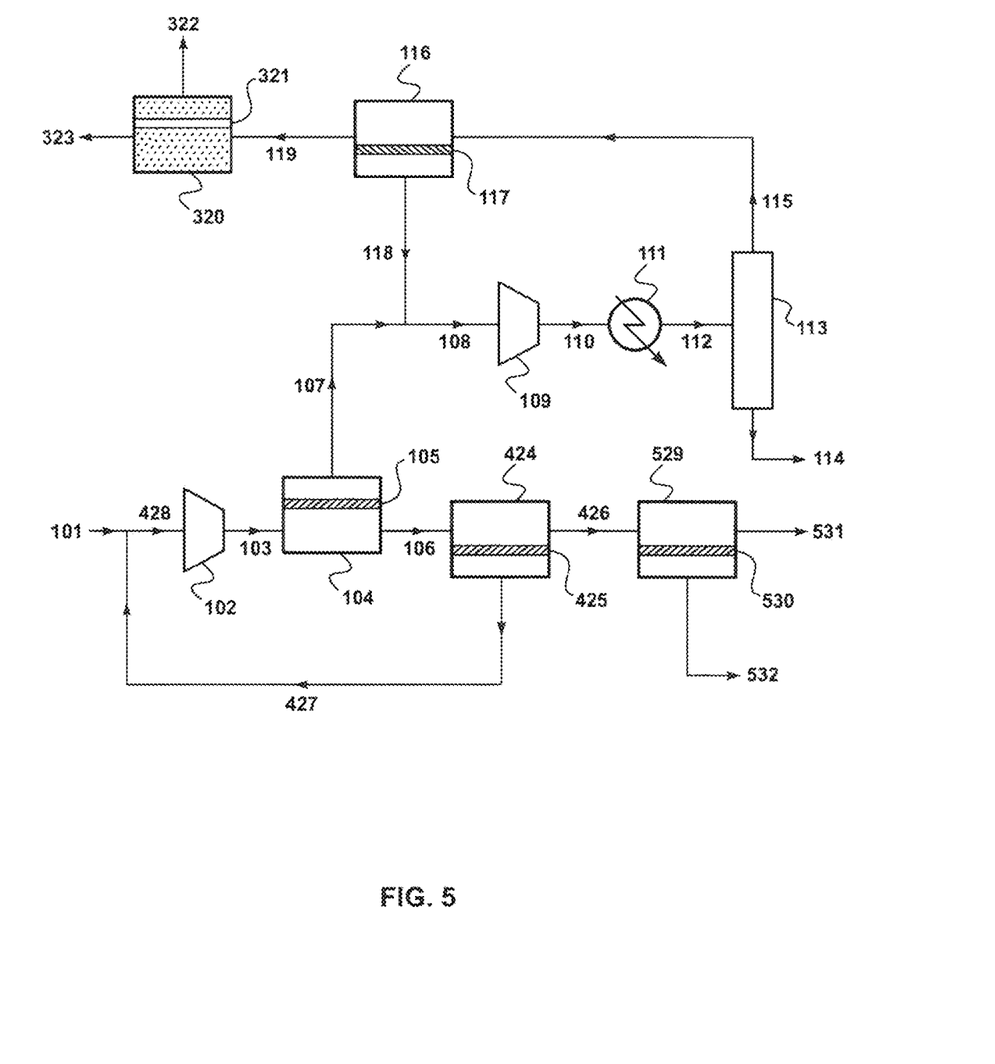
FIG. 5 is a schematic drawing showing a process scheme for a variant of the process of FIG. 4, comprising a fifth membrane separation step for treating the fourth olefin-depleted residue stream of the fourth membrane separation step.

Another embodiment of the olefin recovery process is shown in FIG. 5. This embodiment is similar to that of FIG. 4 in that stream 103, first residue streams 106, uncondensed gas stream 115, and second residue stream 119 all undergo membrane separation. However, in this embodiment fourth residue stream 426 is further treated by a fifth membrane separation step, 529.

Stream 426 is sent as a feed stream across the feed side of membrane(s) 530 that is selectively permeable to olefins, and optionally paraffins, over inorganic gases. A fifth residue stream, 531, depleted in olefin compared with stream 426, is withdrawn from the feed side of the membrane. This stream typically contains a high percentage of the third gas, such as nitrogen, hydrogen, or methane and may be sent to any desired destination within or outside of the manufacturing operation, or simply vented or purged. A fifth permeate stream, 532, enriched in olefin compared to stream 426 is withdrawn from the permeate side of the membrane. This stream has an olefin to paraffin ratio that is preferably reduced to about 4:1, or about 1:1, and more preferably below 1:1 so that this stream may be purged from the process or flared with comparatively little loss of olefin.

The membrane or membranes used for membrane separation step 529 may be similar to the polymeric or inorganic membranes described above.

However, in some embodiments, the fifth membrane, 530, may be selectively permeable to the third gas, such as nitrogen, over olefins and paraffins and other gases. In this case, particularly preferred membrane materials for the membranes selective in favor of the third gas include but are not limited to amorphous homopolymers of perfluorinated dioxole, dioxolanes or cyclic alkyl ethers, or copolymers of these with tetrafluoroethylene.

Thus, in these embodiments, the fifth membrane separation step, 529, produces a fifth permeate stream, 532, that is enriched in nitrogen, for example, compared to stream 426 and a fifth residue stream, 531, that is depleted in nitrogen compared to stream 426. Stream 531 has an olefin to paraffin ratio that is preferably reduced to about 4:1, or about 1:1, and more preferably below 1:1 so that this stream may be purged from the process or flared with comparatively little loss of olefin.

Figure 6:
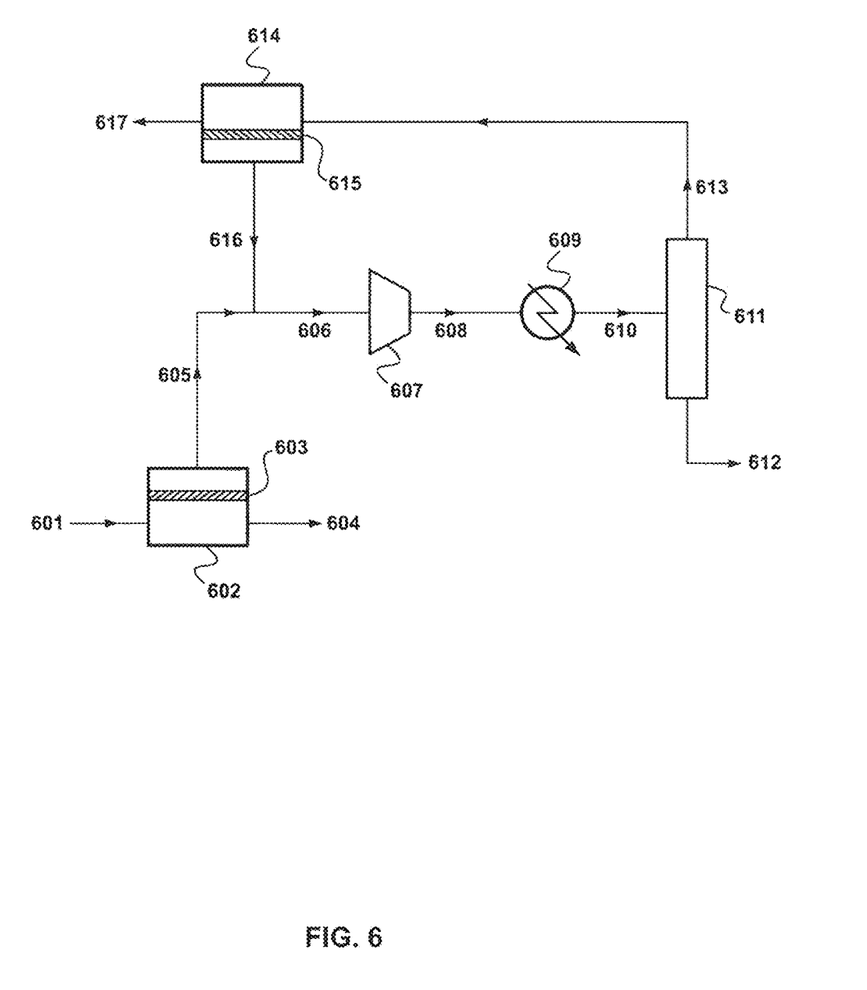
FIG. 6 is a schematic drawing showing an olefin recovery process where the source of the feed gas is already at high pressure according to a basic embodiment of the invention.

An alternative embodiment of the olefin recovery process is shown in FIG. 6. Here, an effluent gas stream, 601, is at a high enough pressure coming from a non-polymeric olefin derivative manufacturing operation that no compression is needed. Thus, stream 601 can be sent directly to a first membrane separation step, 602. Step 602 is carried out in a membrane unit containing membrane(s), 603, made with any suitable material that selectively permeates olefin, and optionally paraffin, over inorganic gases. The membrane or membranes used for step 602 may be similar to the polymeric or inorganic membranes described above for step 104 of FIG. 1.

The first olefin-enriched permeate stream, 605, is mixed with a second olefin-enriched permeate stream, 616, to produce combined stream 606. This stream is sent to a compression step, 607, which produces compressed stream 608. It is preferred that the pressure to which stream 601 is raised be no more than about 30 bara, and more preferably no more than about 25 bara Stream 608 is then passed to a condensation step, 609. The condensation step includes cooling of stream 608 to below the olefin dewpoint temperature, such that a major portion of the olefin is condensed, followed by separation of the resulting liquid and gas phases. Cooling may be performed in any manner, and in one or more sub-steps, including, but not limited to, simple air or water aftercooling of the compressor outlet gases, heat exchange against other on-site process streams, chilling by external refrigerants, and any combinations of these. Preferably, this step should cool stream 608 to a temperature no lower than −40° C., and yet more preferably to no colder than about −35° C.

The liquid and gas phases that are formed by compression and cooling are separated by conventional means in a simple phase separator, knock-out drum or the like, 611, to yield condensed, liquid stream, 612, and uncondensed gas stream, 613. The condensed liquid stream 612 typically comprises 80 mol %, 90 mol %, or more olefin and paraffin.

Uncondensed gas stream, 613, is depleted in olefin and paraffin and is sent for treatment to a second membrane separation step, 614. Prior to this, it may be desirable to heat stream 613 to recover heat and/or to have optimal operating temperatures. Heating of stream 613 may be accomplished by in any way, for example by heat exchange against other on-site process stream or with steam. In FIG. 6, the heat exchange may occur between hot compressed gas stream 608 and cold uncondensed gas stream 613.

The membrane or membranes, 615, to be used in step 614 are made of any material suitable for selectively permeating olefins over paraffins and inorganic gases. Preferred membrane materials are similar to the polymeric and inorganic membranes that can be used in the first membrane separation step, 104, as described above.

Stream 613 flows across the feed side of membrane 615. A second residue stream, 617, that is depleted in olefins, and optionally paraffins, relative to stream 613, is withdrawn from the feed side of the membrane. This stream typically contains a high percentage of the third gas, such as nitrogen, hydrogen, or methane and may be sent to any desired destination within or outside of the manufacturing operation, or simply vented or purged. The second permeate stream, 616, is enriched in olefins, and optionally paraffins, compared with the membrane feed stream. Stream 616 is recycled and combined with the first olefin-enriched permeate stream, 605, upstream of compression step 607.

The invention is now further described by the following examples, which are intended to be illustrative of the invention, but are not intended to limit the scope or underlying principles in any way.

EXAMPLES

Example 1

Olefin Recovery Process in Accordance with the Invention of FIG. 2

A calculation was performed to model the performance of the process of FIG. 2 in treating an effluent stream withdrawn from an olefin manufacturing operation.

For the calculation, the effluent gas stream was assumed to have a flow rate of 1,139 kg/hour and contain propylene, propane, and nitrogen. It was also assumed that the molar compositions were approximately as follows:

Nitrogen: 75.9%
Propylene: 20.8%
Propane: 3.3%

It was further assumed that the effluent gas stream was compressed to 10 bara in first compression step 102 and 22 bara in second compression step 109. The first compressed gas stream 103 and the uncondensed gas stream 115 were separated using polymeric membranes selective for $C_{2+}$ hydrocarbons over other gases in membrane separation steps 104 and 116, respectively. Uncondensed stream 115 was heated to 80° C. prior to membrane separation step 116. It was also assumed that the membrane used in separation step 221 was an inorganic membrane selective for olefin over paraffin. Membrane separation of the condensate in step 221 occurred under vapor permeation conditions.

The calculation was performed using differential element membrane code written at MTR and incorporated into a computer process simulation program (ChemCad 6.3, ChemStations, Austin, Tex.).

The results of the calculations are shown in Table 1.

TABLE 1

| Stream | 101 | 103 | 106 | 107 | 108 | 112 | 115 | 118 | 119 | 220 | 223 | 224 |
|---|---|---|---|---|---|---|---|---|---|---|---|---|
| Total Mass flow (kg/h) | 1,139 | 1,139 | 233 | 906 | 3,426 | 3,426 | 3,105 | 2,521 | 585 | 321 | 278 | 43 |
| Temp (° C.) | 70 | 80 | 75 | 78 | 67 | 35 | 80 | 64 | 49 | 35 | 63 | 46 |
| Pressure (bara) | 1 | 10 | 10 | 1 | 1 | 22 | 22 | 1 | 22 | 22 | 1 | 22 |
| Component (mol %) | | | | | | | | | | | | |
| Nitrogen | 75.9 | 75.9 | 99.0 | 69.1 | 23.5 | 23.5 | 25.6 | 2.5 | 94.5 | 1.5 | 0.1 | 10.6 |
| Propylene | 20.8 | 20.8 | 0.9 | 26.7 | 74.0 | 74.0 | 72.0 | 95.8 | 1.0 | 95.0 | 99.0 | 69.3 |
| Propane | 3.3 | 3.3 | 0.1 | 4.2 | 2.5 | 2.5 | 2.4 | 1.7 | 4.5 | 3.5 | 0.9 | 20.1 |
| Mass flow (in kg/h) | | | | | | | | | | | | |
| Nitrogen | 770 | 770 | 230 | 540 | 582 | 582 | 579 | 42 | 537 | 3 | 0 | 3 |
| Propylene | 317 | 317 | 3 | 314 | 2,746 | 2,746 | 2,440 | 2,432 | 8 | 305 | 275 | 31 |
| Propane | 52 | 52 | 0 | 52 | 99 | 99 | 87 | 47 | 40 | 12 | 3 | 9 |

The process achieves an olefin recovery of 86.7%. Stream 223 has a propylene purity of about 99%. In addition, the olefin to paraffin ratio in purge/residue stream 224 is reduced to about 3:1 from 6:1 in effluent stream 101.

Example 2

Olefin Recovery Process in Accordance with the Invention of FIG. 3

A calculation was performed to model the performance of the process of FIG. 3 in treating an effluent gas stream withdrawn from an olefin manufacturing operation. It was assumed that the process conditions and molar composition of the effluent gas stream were similar to those in Example 1, however, polymeric membranes selective for $C_{2+}$ hydrocarbons over other gases were used in steps 104 and 320 while an inorganic membrane selective for olefins and paraffins was used in step 116.

The results of the calculations are shown in Table 2.

The process achieves an olefin recovery of 96.4% with a propylene purity in stream 114 of about 95%. The olefin to paraffin ratio in purge/flare stream 322 was reduced to about 1:4.

Example 3

Olefin Recovery Process in Accordance with the Invention of FIG. 5, Using a $C_{2+}$ Hydrocarbon-Selective Membrane in the Fifth Membrane Separation Step A calculation was performed to model the performance of the process of FIG. 5 in treating an effluent stream withdrawn from an olefin manufacturing operation. It was assumed that the process conditions and molar composition of the effluent gas stream were similar to those in Example 1, however, inorganic membranes selective for olefins over paraffins were used in steps 104 and 116, and polymeric membranes selective, for hydrocarbons over other gases were used in steps 320, 424, and 529.

TABLE 2

| Stream | 101 | 103 | 106 | 107 | 108 | 112 | 114 | 115 | 118 | 119 | 322 | 323 |
|---|---|---|---|---|---|---|---|---|---|---|---|---|
| Total Mass flow (kg/h) | 1,139 | 1,139 | 233 | 906 | 3,426 | 3,426 | 321 | 3,106 | 2,521 | 585 | 355 | 230 |
| Temp (° C.) | 70 | 80 | 75 | 78 | 67 | 35 | 35 | 80 | 64 | 49 | 46 | 47 |
| Pressure (bara) | 1 | 10 | 10 | 1 | 1 | 22 | 22 | 22 | 1 | 22 | 1 | 22 |
| Component (mol %) | | | | | | | | | | | | |
| Nitrogen | 75.9 | 76.0 | 99.0 | 69.0 | 23.5 | 23.5 | 1.5 | 25.6 | 2.5 | 94.5 | 99.0 | 87.2 |
| Propylene | 20.8 | 20.8 | 0.9 | 26.7 | 73.9 | 73.9 | 94.9 | 71.9 | 95.8 | 1.0 | 0.2 | 2.3 |
| Propane | 3.3 | 3.3 | 0.1 | 4.2 | 2.5 | 2.5 | 3.5 | 2.4 | 1.8 | 4.5 | 0.8 | 10.5 |
| Mass flow (in kg/h) | | | | | | | | | | | | |
| Nitrogen | 770 | 770 | 230 | 540 | 582 | 582 | 3.3 | 579 | 42 | 537 | 350 | 187 |
| Propylene | 317 | 317 | 3 | 314 | 2,746 | 2,746 | 305 | 2,440 | 2,432 | 8 | 1 | 7 |
| Propane | 52 | 52 | 0 | 52 | 99 | 99 | 12 | 87 | 47 | 40 | 4 | 35 |

The results of the calculations are shown in Table 3.

TABLE 3

| Stream | 101 | 428 | 103 | 106 | 107 | 108 | 112 | 114 | 115 | 426 | 427 | 531 | 532 |
|---|---|---|---|---|---|---|---|---|---|---|---|---|---|
| Total Mass flow (kg/h) | 1,139 | 1,822 | 1,822 | 1,405 | 417 | 765 | 765 | 348 | 418 | 722 | 683 | 530 | 191 |
| Temp (° C.) | 70 | 73 | 80 | 78 | 79 | 72 | 35 | 35 | 80 | 77 | 78 | 76 | 77 |
| Pressure (bara) | 1 | 1 | 10 | 10 | 1 | 1 | 22 | 22 | 22 | 10 | 1 | 10 | 1 |
| Component (mol %) | | | | | | | | | | | | | |
| Nitrogen | 75.9 | 79.2 | 79.2 | 91.7 | 22.8 | 15.5 | 15.5 | 1.6 | 26.1 | 98.2 | 84.4 | 99.0 | 95.8 |
| Propylene | 20.8 | 16.2 | 16.2 | 4.7 | 68.0 | 75.6 | 75.6 | 87.8 | 66.6 | 1.0 | 8.9 | 0.6 | 2.4 |
| Propane | 3.3 | 4.6 | 4.6 | 3.5 | 9.2 | 8.7 | 8.7 | 10.6 | 7.3 | 0.8 | 6.7 | 0.4 | 1.8 |
| Mass flow (in kg/h) | | | | | | | | | | | | | |
| Nitrogen | 770 | 1,302 | 1,302 | 1,234 | 68 | 83 | 83 | 4 | 79 | 702 | 532 | 522 | 179 |
| Propylene | 317 | 401 | 401 | 95 | 306 | 609 | 609 | 305 | 303 | 11 | 84 | 4 | 7 |
| Propane | 52 | 119 | 119 | 75 | 43 | 73 | 73 | 39 | 35 | 9 | 66 | 4 | 5 |

The process achieves an olefin recovery of 96.4% with a propylene purity in stream 114 of about 88%. The olefin to paraffin ratio in purge/flare streams 322 and 532 were reduced to about 1:4 (from Example 2) and about 1.4:1, respectively.

Example 4

Olefin Recovery Process in Accordance with the Invention of FIG. 5, Using a Nitrogen-Selective Membrane in the Fifth Membrane Separation Step A calculation was performed to model the performance of the process of FIG. 5 in treating an effluent stream withdrawn from an olefin manufacturing operation.

For the calculation, the effluent gas stream was assumed to have a flow rate of 1,140 kg/hour and contain propylene, propane, and nitrogen. It was also assumed that the molar compositions were approximately as follows:

Nitrogen: 76.0%
Propylene: 27.8%
Propane: 4.6%

It was further assumed that the effluent gas stream, was compressed to 10 bara in first compression step 102 and 22 bara in second compression step 109. Membrane separation steps 104, 116, and 424 used inorganic membranes selective for olefins over paraffins. Membrane separation step 320 used a polymeric membrane selective for $C_{2+}$ hydrocarbons over other gases. Membrane separation step 529 used a membrane selective for nitrogen over other gases. Uncondensed stream 115 was heated to 80° prior to membrane separation step 116.

The calculation was performed using differential element membrane code written at MTR and incorporated into a computer process simulation program (ChemCad 6.3, ChemStations, Austin, Tex.).

The results of the calculations are shown in Table 4.

TABLE 4

| Stream | 101 | 428 | 103 | 106 | 108 | 112 | 114 | 115 | 322 | 426 | 427 | 531 | 532 |
|---|---|---|---|---|---|---|---|---|---|---|---|---|---|
| Total Mass flow (kg/h) | 1,140 | 1,310 | 1,312 | 900 | 700 | 700 | 330 | 370 | 43 | 730 | 170 | 70 | 660 |
| Temp (° C.) | 70 | 71 | 80 | 78 | 73 | 35 | 35 | 80 | 47 | 77 | 77 | 75 | 76 |
| Pressure (bara) | 1 | 1 | 10 | 10 | 1 | 22 | 22 | 22 | 1 | 10 | 1 | 10 | 2 |
| Component (mol %) | | | | | | | | | | | | | |
| Nitrogen | 76.0 | 75.7 | 75.7 | 93.5 | 14.8 | 14.8 | 1.6 | 25.9 | 80.2 | 97.7 | 74.1 | 84.5 | 99.0 |
| Propylene | 27.8 | 20.2 | 20.2 | 3.6 | 79.2 | 79.2 | 91.4 | 69.2 | 2.3 | 0.9 | 16.2 | 5.9 | 0.4 |
| Propane | 4.6 | 4.1 | 4.1 | 2.9 | 6.0 | 6.0 | 7.5 | 4.9 | 17.5 | 1.4 | 9.7 | 9.6 | 0.6 |
| Mass flow (in kg/h) | | | | | | | | | | | | | |
| Nitrogen | 770 | 883 | 883 | 814 | 72 | 72 | 3 | 69 | 31 | 701 | 113 | 55 | 646 |
| Propylene | 317 | 354 | 354 | 47 | 582 | 582 | 306 | 276 | 1 | 10 | 37 | 6 | 4 |
| Propane | 52 | 76 | 76 | 39 | 46 | 46 | 25 | 21 | 11 | 16 | 23 | 10 | 6 |

The process achieves an olefin recovery of 96.5% with a propylene purity in stream 114 of about 91%. The olefin to paraffin ratio in purge/flare streams 322 and 531 were reduced to about 1:11 and about 1:1.6, respectively.

I claim:
1. A process for treating an effluent gas stream arising from an operation that manufactures an olefin or an olefin derivative, said effluent gas stream comprising an olefin, a paraffin and a third gas, the process comprising the steps of:
   (a) compressing said effluent gas stream using a first compressor to produce a first compressed gas stream;
   (b) separating the first compressed stream gas stream using a first membrane to produce a first olefin-enriched permeate stream and a first olefin-depleted residue stream;

(c) compressing the first olefin-enriched permeate stream using a second compressor to produce a second compressed gas stream;

(d) partially condensing the second compressed stream, including cooling and separating the compressed stream into an uncondensed gas stream depleted in olefin and paraffin and a condensed liquid condensate enriched in olefin and paraffin;

(e) separating the uncondensed gas stream using a second membrane to produce a second olefin-enriched permeate stream and a second olefin-depleted residue stream; and (f) returning the second olefin-enriched permeate stream upstream of the second compressor.

2. The process of claim 1, wherein the olefin is selected from the group consisting of ethylene, propylene and butylene.

3. The process of claim 1, wherein the operation is selected from the group consisting of steam cracking, fluid catalytic cracking, propane dehydrogenation, olefin metathesis, a methanol-to-olefin process, a methanol-to-propylene process, polyolefin manufacturing, chlorohydrin production, butyraldehyde, oxo alcohol production, isopropyl alcohol production, acrylic acid production, allyl chloride production, acrylonitrile production, cumene production, ethylene oxide production, vinyl acetate production, ethylene dichloride production, ethanol production, and ethylbenzene production.

4. The process of claim 1, wherein the third gas is nitrogen.

5. The process of claim 1, wherein the first membrane is an inorganic membrane.

6. The process of claim 1, wherein the second membrane is a polymeric membrane or an inorganic membrane.

7. The process of claim 1, further comprising the step of:

(g) separating the condensed liquid condensate using a third membrane to produce a third olefin-enriched permeate stream and a third olefin-depleted residue stream.

8. The process of claim 7, wherein the third membrane is an inorganic membrane.

9. The process of claim 7, wherein the condensed liquid condensate is revaporized prior to step (g).

10. The process of claim 1, further comprising the step of:

(g) separating the second olefin-depleted residue stream using a third membrane to produce a third olefin-enriched permeate stream and third olefin-depleted residue stream.

11. The process of claim 10, wherein the third membrane is a polymeric membrane.

12. The process of claim 1, further comprising the steps of:

(f) separating the first olefin-depleted residue stream using a third membrane to produce a third olefin-enriched permeate stream and a third olefin-depleted residue stream; and (g) returning the third olefin-enriched permeate stream upstream of the first compressor.

13. The process of claim 10, further comprising the step of:

(h) separating the first olefin-depleted residue stream using a fourth membrane to produce a fourth olefin-enriched permeate stream, and a fourth olefin-depleted residue stream; and (i) returning the fourth olefin-enriched permeate stream upstream of the first compressor.

14. The process of claims 12 or 13, wherein the third or fourth membrane, respectively, is a polymeric or inorganic membrane.

15. The process of claim 12, further comprising the step of:

(h) separating the third olefin-depleted residue stream using a fourth membrane to produce a fourth olefin-enriched permeate stream and a fourth olefin-depleted residue stream.

16. The process of claim 13, further comprising the step of:

(j) separating the fourth olefin-depleted residue stream using a fifth membrane to produce a fifth olefin-enriched permeate stream and a fifth olefin-depleted residue stream.

17. The process of claims 15 or 16, wherein the fourth or fifth membrane, respectively, is a polymeric or inorganic membrane.

18. The process of claim 15, further comprising the step of:

(j) separating the fourth olefin-depleted residue stream using a fifth membrane to produce a nitrogen-enriched permeate stream and a nitrogen-depleted residue stream.

19. A process for treating an effluent gas stream arising from an operation that manufactures an olefin or an olefin derivative, said effluent gas stream comprising an olefin, a paraffin and a third gas, the process comprising the steps of:

(a) separating the effluent stream gas stream using a first membrane to produce a first olefin-enriched permeate stream and a first olefin-depleted residue stream;

(b) compressing the first olefin-enriched permeate stream using a first compressor to produce a first compressed gas-stream;

(c) partially condensing the compressed stream, including cooling and separating the compressed stream into an uncondensed gas stream depleted in olefin and paraffin and a condensed liquid condensate enriched in olefin and paraffin; and (d) separating the uncondensed gas stream using a second membrane to produce a second olefin-enriched permeate stream and a second olefin-depleted residue stream; and (e) returning the second olefin-enriched permeate stream upstream of the compressor.

20. The process of claim 19, wherein the olefin is selected from the group consisting of ethylene, propylene and butylene.

21. The process of claim 19, wherein the operation is selected from the group consisting of steam cracking, fluid catalytic cracking, propane dehydrogenation, olefin metathesis, a methanol-to-olefin process, a methanol-to-propylene process, polyolefin manufacturing, chlorohydrin production, butyraldehyde, oxo alcohol production, isopropyl alcohol production, acrylic acid production, allyl chloride production, acrylonitrile production, cumene production, ethylene oxide production, vinyl acetate production, ethylene dichloride production, ethanol production, and ethylbenzene production.

22. The process of claim 19, wherein the third gas is nitrogen.

23. The process of claim 19, wherein the first membrane is an inorganic membrane.

24. The process of claim 19, further comprising the steps of:

(f) separating the first olefin-depleted residue stream using a third membrane to produce a third olefin-enriched permeate stream and a third olefin-depleted residue stream;

(g) compressing the third olefin-enriched permeate stream using a second compressor to produce a second compressed gas stream; and (h) returning the second compressed gas stream upstream of step (a).

* * * * *